(12) United States Patent
Connelly et al.

(10) Patent No.: US 9,526,439 B2
(45) Date of Patent: Dec. 27, 2016

(54) WOUND DRESSINGS AND PERFORMANCE MEASUREMENT OF SUCH DRESSINGS

(75) Inventors: Patricia Connelly, Glasgow (GB); David McColl, Glasgow (GB)

(73) Assignee: University of Strathclyde, Glasgow (GB)

(*) Notice: Subject to any disclaimer, the term of this patent is extended or adjusted under 35 U.S.C. 154(b) by 1519 days.

(21) Appl. No.: 11/578,526

(22) PCT Filed: Apr. 18, 2005

(86) PCT No.: PCT/GB2005/001483
§ 371 (c)(1),
(2), (4) Date: Mar. 18, 2008

(87) PCT Pub. No.: WO2005/099644
PCT Pub. Date: Oct. 27, 2005

(65) Prior Publication Data
US 2008/0171957 A1    Jul. 17, 2008

(30) Foreign Application Priority Data

Apr. 16, 2004 (GB) .................................. 0408492.7

(51) Int. Cl.
*A61F 13/42* (2006.01)
*A61F 13/02* (2006.01)
(Continued)

(52) U.S. Cl.
CPC ............ *A61B 5/0531* (2013.01); *A61B 5/445* (2013.01); *A61F 13/00* (2013.01); *A61F 13/42* (2013.01);
(Continued)

(58) Field of Classification Search
CPC .... A61F 13/00; A61F 13/00051; A61F 13/02; A61F 2013/00361; A61F 2013/00429; A61F 2013/00442; A61F 2013/0094; A61F 2013/00944; A61F 2013/00961; A61F 13/00055; A61F 13/42; A61F 5/445; A61B 5/05; A61B 5/053; A61B 5/0531; A61B 5/44; A61B 5/441; A61B 5/445; A61N 1/04; A61N 1/0404; A61N 1/0484; A61N 1/0492; A61L 15/56; A61L 24/00
(Continued)

(56) References Cited

U.S. PATENT DOCUMENTS 4,352,059 A * 9/1982 Suh et al. ................. 324/659
4,580,233 A * 4/1986 Parker et al. ................ 73/73
(Continued)

FOREIGN PATENT DOCUMENTS

DE    3223036    12/1983
DE    4014572    11/1991
(Continued)

OTHER PUBLICATIONS

Office Action dated Jun. 6, 2010 of corresponding European Patent Application No. 05 738 126.1-2319.
(Continued)

*Primary Examiner* — Alireza Nia
*Assistant Examiner* — Keri J Nelson
(74) *Attorney, Agent, or Firm* — Alston & Bird LLP

(57) ABSTRACT

A wound dressing (10) including a plurality of discrete, spaced apart pairs of electrodes (18a, 18b) for allowing an electrical property or characteristic of the dressing (10) to be measured. By measuring an electrical characteristic of the dressing, such as the impedance, the hydration thereof can be determined and monitored.

15 Claims, 8 Drawing Sheets

(51) Int. Cl.
*A61L 15/56* (2006.01)
*A61B 5/053* (2006.01)
*A61B 5/00* (2006.01)
*A61F 13/00* (2006.01)

(52) U.S. Cl.
CPC .......... *A61L 15/56* (2013.01); *A61F 13/00051* (2013.01); *A61F 2013/00429* (2013.01); *A61F 2013/00442* (2013.01); *A61F 2013/00944* (2013.01); *A61F 2013/00961* (2013.01)

(58) Field of Classification Search
USPC .... 602/2, 41–43, 48; 600/15, 382, 390, 393, 600/547; 607/2, 115, 148–152; 73/29.01, 73/335.02, 335.03; 324/634, 640, 643, 664, 324/689, 694; 604/361
See application file for complete search history.

(56) References Cited

U.S. PATENT DOCUMENTS

| | | | |
|---|---|---|---|
| 5,218,973 A * | 6/1993 | Weaver et al. | 607/152 |
| 6,200,250 B1 | 3/2001 | Janszen | |
| 6,411,853 B1 * | 6/2002 | Millot et al. | 607/50 |
| 2002/0034492 A1 * | 3/2002 | Munro et al. | 424/78.36 |
| 2002/0091347 A1 | 7/2002 | Eakin | |
| 2002/0176885 A1 | 11/2002 | Najafi et al. | |
| 2002/0198483 A1 | 12/2002 | Wariar et al. | |
| 2003/0216783 A1 * | 11/2003 | Lehtoluoto | 607/2 |
| 2004/0036484 A1 | 2/2004 | Tamai | |
| 2004/0230172 A1 * | 11/2004 | Shapira | 604/361 |

FOREIGN PATENT DOCUMENTS

| | | |
|---|---|---|
| GB | 2362466 | 11/2001 |
| JP | 9-33468 | 7/1997 |
| JP | 10-295726 | 11/1998 |
| JP | 2001-515762 A | 9/2001 |
| JP | 2002224093 | 8/2002 |
| JP | 2003-520820 A | 7/2003 |
| JP | 2004-85277 | 3/2004 |
| WO | WO 90/05026 | 5/1990 |
| WO | WO 2004/049937 | 6/2004 |

OTHER PUBLICATIONS

International Search Report for International Application No. PCT/GB2005/001483 completed Oct. 10, 2005.
International Preliminary Report on Patentability for International Application No. PCT/GB2005/001483 completed Jul. 17, 2006.
Japan Patent Office, Appeal Examiner's First Office Action for Appeal No. 2011-15910 (Application No. 2007-507852), dated Jun. 25, 2012, 2 pages, Japan.
Pethig, Ronald, et al., "Review Article: The Passive Electrical Properties of Biological Systems: Their Significance in Physiology, Biophysics and Biotechnology," Phys. Med. Biol., 1987, pp. 933-970, vol. 32, No. 8, IOP Publishing Ltd, UK.
Agilent Technologies, Inc., "Agilent Basics of Measuring the Dielectric Properties of Materials, Application Note," Jun. 26, 2006, Agilent Technologies, Inc., USA.

* cited by examiner $$Z' = \frac{R}{1+\omega^2 C^2 R^2} + R + \frac{R}{1+\omega^2 C^2 R^2}$$

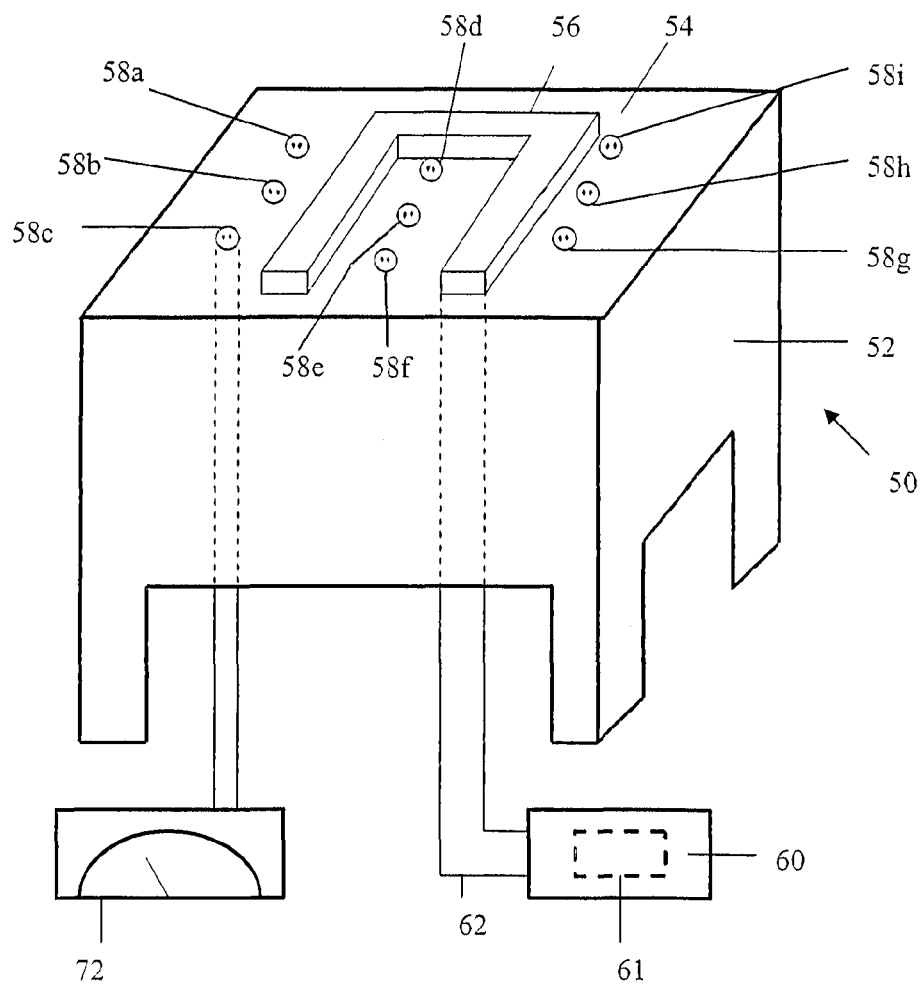
Figure 7
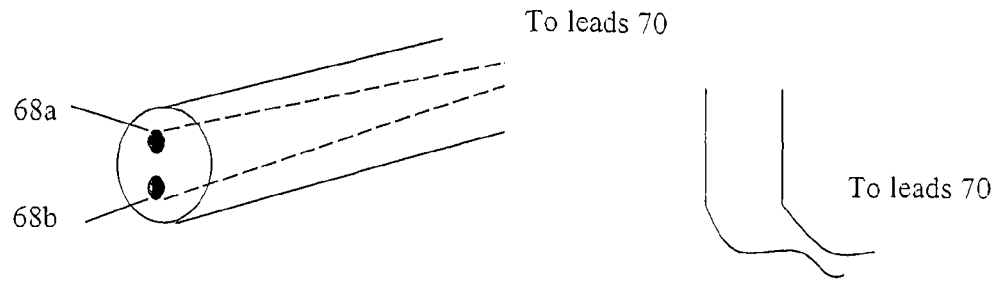
Figure 8a
Figure 8b

| | 0 hours | 1 hour | 4 hours | 8 hours | 12 hours | 16 hours | 20 hours | 24 hours |
|---|---|---|---|---|---|---|---|---|
| V1 | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 | 8 4 3<br>7 T 2<br>6 5 1 | 8 4 3<br>7 T 2<br>6 5 1 | 8 4 3<br>7 T 2<br>6 5 1 |
| V2 | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 | 8 4 3<br>7 T 2<br>6 5 1 | 8 4 3<br>7 T 2<br>6 5 1 | 8 4 3<br>7 T 2<br>6 5 1 |
| V3 | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 | 8 4 3<br>7 T 2<br>6 5 1 | 8 4 3<br>7 T 2<br>6 5 1 | 8 4 3<br>7 T 2<br>6 5 1 |
| V4 | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 | 8 4 3<br>7 T 2<br>6 5 1 | 8 4 3<br>7 T 2<br>6 5 1 | 8 4 3<br>7 T 2<br>6 5 1 |
| V5 | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 | 8 4 3<br>7 T 2<br>6 5 1 | 8 4 3<br>7 T 2<br>6 5 1 | 8 4 3<br>7 T 2<br>6 5 1 |

| Code | |
|---|---|
| Wet | |
| Moist | |
| Dry | |
| Fluid in | F |
| Temp | T |

Figure 10

|   | 0 hours | 1 hour | 4 hours | 8 hours | 12 hours | 16 hours | 20 hours | 24 hours |
|---|---|---|---|---|---|---|---|---|
| T1 | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 | 8/4/3<br>7/T/2/<br>6/5/1/ | 8/4/3<br>7/T/2/<br>6/5/1/ |
| T2 | 8 4 3<br>7 T 2<br>6 5 1 F | 8 4 3<br>7 T 2<br>6 5 1 F | 8 4 3<br>7 T 2<br>6/5/1 F | 8 /4/ 3<br>7 T 2<br>6/5/ 1 F | 8/4/ 3<br>7 T 2<br>6/5/1/ | 8/4/ 3<br>7 T 2<br>6/5/1/ | 8/4/ 3<br>7 T 2/<br>6/5/1/ | 8/4/ 3<br>7 T 2/<br>6/5/1/ |
| T3 | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 F | 8 4 3<br>7 T 2<br>6 5 1 | 8 4 3<br>7 T 2<br>6 5 1 | 8/4/3/<br>7/T/2/<br>6/5/1/ | 8/4/3/<br>7/T/2/<br>6/5/1/ |
| T4 | 8 4 3<br>7 T 2<br>6 5 1 F | 8 4 3<br>7 T 2<br>6 5 1 F | 8 4 3<br>7 T 2<br>6 5 1 F | 8 4 /3/<br>7 T 2<br>6 5 1 F | 8 4 /3/<br>7/T 2<br>6 5 1 | 8/4/3/<br>7/T 2/<br>6/5/1/ | 8/4/3/<br>7/T 2/<br>6/5/1/ | 8 4/3/<br>7/T 2/<br>6/5/1/ |
| T5 | 8 4 3<br>7 T 2<br>6 5 1 F | 8 /4/ 3<br>7 T 2<br>6 /5/ 1 F | 8/4/3/<br>7/T 2<br>6/5/1 F | 8/4/3/<br>7/T 2<br>6/5/1 F | 8/4/3/<br>7/T 2<br>6/5/1 | 8/4/3/<br>7/T 2/<br>6/5/1/ | 8/4/3/<br>7/T 2/<br>6/5/1/ | 8/4/3/<br>7/T 2/<br>6/5/1/ |

| Code | |
|---|---|
| Wet | |
| Moist | . |
| Dry | / |
| Fluid in | F |
| Temp | T |

Figure 11

WOUND DRESSINGS AND PERFORMANCE MEASUREMENT OF SUCH DRESSINGS

The present invention relates to a wound dressing, the hydration of which can be measured in use. In addition, the invention relates to a test rig for measuring the performance of a wound dressing, in particular for measuring the hydration of such a dressing and monitoring the wound dressing/wound interface.

Conventional wound dressings are designed to remove exudates from wound sites and maintain a warm and humid wound environment to improve the rate of healing. A problem with most known dressings is that short of removing a dressing and checking the wound it is generally not possible to monitor whether the dressing is providing a suitably moist environment for optimal wound healing or to assess the condition of the interface between the wound and the wound dressing. Hence, there is a need in the art for a dressing that can be used in situ to provide an indication of the condition of the wound/wound dressing interface.

EP 0,403,608 A describes a dressing for sensing the condition of a wound in situ. In one example, the dressing includes temperature sensitive colour change materials. Temperature changes can be related a number of parameters such as blood flow to the skin or presence of infection. Hence, a change of colour is indicative of a change in condition. In an alternative embodiment EP 0,403,608 A describes a dressing that includes a moisture detector. However, there is no description of how this could be implemented.

WO2004/049937 takes a different approach to that of EP 0,403,608 A. Rather than measuring the condition of a wound dressing, this publication describes a dressing that is adapted to measure the condition of a wound/wound dressing interface by directly measuring the wound, and not the dressing. To do this, a plurality of electrodes is provided on a skin contact surface of the dressing. Typically, these are printed onto a solid polymer film. Gel has to be applied to these electrodes for making contact with underlying skin. The dressing is arranged so that in use the electrical resistance between the electrodes via the dressing is high relative to the resistance via the gel between each electrode and the underlying tissue. In this way, when the dressing is applied to a patient, the resistance of the wound can be measured and not the resistance of the dressing. A problem with this technique is that the depth of penetration of the electric field into the tissue is not known and so there is no measure or indication of what is the current path. Hence, quantifying what exactly is being measured is difficult. This means that analysing the results can be problematic. Also, because the electrodes are printed onto a polymer film, this makes them unsuitable for use in a moisture balance dressing, because it does not allow the gradual spreading of hydration through the dressing.

According to one aspect of the present invention there is provided a wound dressing including an array of pairs of elements or electrodes for allowing a localised measure of an electrical property or characteristic, such as impedance, of the dressing to be obtained.

By pairing the electrodes, the current path between them is clearly defined, which means that the impedance of the dressing can be accurately measured and mapped in situ in a localised manner. This allows analysis of the moisture in the wound environment to be made without removal of the dressing being necessary. Information gathered from passing direct and alternating current (including cyclic voltammetry) through the elements allows the analysis of elements of the fluid in the dressing.

Using the dressing in which the invention is embodied makes it possible to monitor the status of hydration of a wound environment through the stages: dry, non-optimal (for healing) to wet, optimal (for healing). The hydration status can be linked to four stages of wound healing and specific rates of release of wound exudate. In simple terms this can be translated to 'change dressing' or 'leave dressing in place' instructions for a carer and more sophisticated information for a clinical user.

The elements or electrodes may be embedded within the dressing. Alternatively or additionally, the elements or electrodes may be mounted on the surface of the dressing. Having the elements distributed on the surface of the dressing and embedded within the body of the dressing allows information to be collected that can be used to generate a three-dimensional moisture distribution or analysis of fluid constituents within and across the dressing.

The dressing may comprise a plurality of adjacent layers. The elements may be embedded between adjacent layers. The elements may be fully embedded in the dressing during the manufacturing process. The elements may be wire or printed electrodes. The electrodes may be silver/silver chloride electrodes. The elements may include terminals adapted to be connected to an electrical impedance meter or electrochemical analysis instrument.

The sensor array may be arranged so that a potential current flow path is provided between paired electrodes, but substantially no current flow path exists between pairs of electrodes. An advantage of this is that there is substantially no measurement overlap and the regions of the dressing that are being measured are very well defined.

According to another aspect of the invention there is provided a meter or electrochemical analysis instrument adapted for use with the dressing of the previous aspect to measure an electrical characteristic, such as the impedance, of the dressing or the constituents of the fluid in the dressing.

The meter or instrument may include electrodes adapted to be connected to terminals on the dressing. Optionally, for ease of use the meter or instrument may be a handheld meter or instrument.

The meter or instrument may be disposable. This has the advantage of preventing infection from one patient being transmitted to another patient through the meter. Alternatively, the meter or instrument may be easily cleaned or sterilised.

The meter may be programmed or configured to give an indication of whether the dressing requires changing or the status of the wound. Such an indication can be provided based on readings obtained in test results.

According to yet another aspect of the present invention there is provided a method for measuring wound dressing hydration comprising measuring an electrical characteristic of the dressing, such as the impedance at a plurality of predetermined locations on the dressing.

The method may further involve comparing the measured characteristic with a predetermined characteristic and analysing the constituents of the fluid in the wound dressing or the clinical status of the wound to wound dressing interface using the results of the step of comparing.

According still another aspect of the present invention there is provided a test rig for testing the performance of a wound dressing or a model wound/wound dressing interface and including: a test bed having a surface adapted to receive a dressing or a model wound/wound dressing interface, supply means for supplying a fluid to the test bed, and monitoring means for monitoring an electrical property, such as impedance, of a dressing or a model wound/wound dressing interface on the test bed.

By measuring the impedance of a wound dressing using the test rig, the level of moisture in the dressing can be measured and used to predict the performance of the dressing in use, as well as its ability to maintain a moist and humid wound environment for efficient wound healing. By monitoring the impedance as a function of time, the moisture levels at the wound interface may be tracked and mapped, thereby providing an indication of the dressing performance.

The test bed surface may include one or more channels thereon. Each channel can be any form of groove or receptacle, which in use is in fluid communication with the fluid supply means. The provision of a channel in the surface of the test bed allows the supplied fluid to reach different areas of a dressing. The channel simulates an actual wound.

The channel may have a serpentine form. An advantage of this is that it maximises the surface area of the dressing that the supplied fluid can reach in a test, establishing rigorous conditions for the test.

The supply means may be operable to supply fluid at a variable rate to the test bed. Supplying fluid at a variable rate to the test bed channel is preferred as, in reality, wounds exude exudate at a variable rate. Alternatively, the supply means may be operable to supply fluid at a constant rate. This may make comparison of different dressings easier.

A plurality of monitoring means may be provided. This is useful because it can be desirable to measure the impedance in a number of locations on the surface of, or in the body of, the dressing. Providing a plurality of monitoring means allows a spatial distribution of moisture to be determined at a given point in time.

The monitoring means may be operable to use an alternating current to measure the impedance of the dressing. Any frequency of alternating current may be selected. In some circumstances, it may be of interest to study the electrochemistry, in which case relatively low frequencies in the near dc to a few hundred Hz are preferred. For general monitoring of ionic conductivity or the presence of moisture, frequencies in the kilohertz range are used. Frequencies higher than kilohertz can be used to characterise the sensor electrodes or to look at specific properties of local tissue or dressing. In the main applications of this invention, frequencies in the kilohertz range are most often employed.

Alternatively or additionally, the monitoring means may be operable to use direct current to monitor electrical conductivity of the wound fluid or dressing. The monitoring means may be operable to use both direct and alternating current (including cyclic voltammetry waveforms) contemporaneously to monitor constituents of the wound fluids directly in addition to levels of hydration. In these configurations both d.c and a.c. can be applied together or separately or cyclic voltammetry may be employed. These methods are well known to the skilled electrochemist for fluid analysis but have not previously been available for analysis of wound dressings.

The monitoring means may comprise surface electrodes. The surface electrodes can be encased or printed. In practice, these can be made to be fairly robust. Such electrodes can be used to measure the moisture at different positions across the surface of a dressing. The information gathered from surface electrodes can be used to generate a two dimensional moisture distribution or two-dimensional information on the components of the wound fluid.

Alternatively, the monitoring means may comprise insulated wire electrodes having a non-insulated tip exposing a conducting component. Wire electrodes can be pushed into the dressing to measure the moisture both across and through the dressing. The information gathered from wire electrodes can be used to generate a three-dimensional moisture distribution or three-dimensional information on the constituents of the wound fluid. If wire electrodes are used, the electrodes are preferably silver/silver chloride wire electrodes.

The fluid supplied to the test bed is preferably an ionic fluid and may be of the type commonly used to model physiological fluid or wound exudate.

According to another aspect of the present invention there is provided a method of measuring the performance of a dressing or a model wound interface including: providing a test rig having a test bed, applying a dressing or a model wound interface to the test bed, supplying fluid to the test bed, and monitoring an electrical property, such as impedance, of the dressing or the model wound interface using a plurality of electrodes in contact with the dressing.

Various aspects of the present invention will now be described by way of example only and with reference to the accompanying drawings, of which:

FIG. 7 is a schematic view of a test rig for testing a wound dressing;

FIGS. 8a and 8b show examples of electrode pairs for use in the rig of FIG. 7;

FIG. 10 shows hydrations levels for five hydrofibre dressings measured over a twenty four hour period;

FIG. 11 shows hydrations levels for five foam dressings measured over a twenty four hour period.

The present invention is based on a localised measurement of the hydration of wound dressings at the dressing/wound interface. To do this measurement, a series of paired electrodes is provided on or within the wound dressing.

Figure 1:
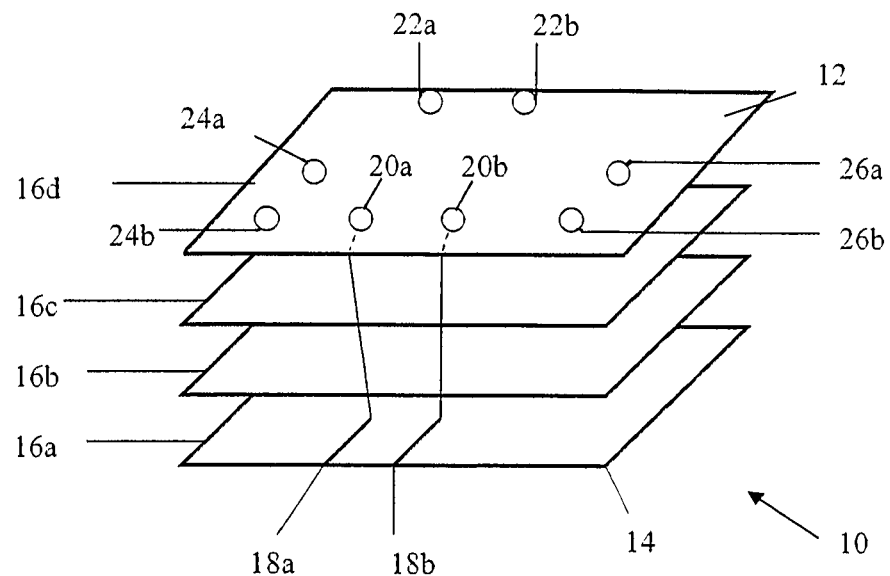
FIG. 1 is a view of a first dressing.

FIG. 1 shows a dressing 10 incorporating a sensor array having a plurality of electrodes suitable for the measurement of impedance in the dressing. The dressing 10 has an upper external surface 12 and a wound contact surface 14. Between the upper external surface 12 and the wound contact surface 14 are four layers of gauze 16a to 16d. Embedded between the wound contact surface 14 and the first gauze layer 16a is an electrode pair 18a, 18b. These electrodes 18a, 18b terminate on the upper external surface 12 at a first pair of terminals 20a, 20b. A second pair of electrodes (not shown) is embedded between the first and second gauze layers 16a, 16b and terminate at a second pair of terminals 22a, 22b. A third pair of electrodes (not shown) is embedded between the second and third gauze layers 16b, 16c and terminate at a third pair of terminals 24a, 24b. A fourth pair of electrodes (not shown) is embedded between the third and fourth gauze layers 16c, 16d, and terminate at a fourth pair of terminals 26a, 26b.

Because the electrodes of FIG. 1 are paired for the purposes of measuring the impedance of the dressing, the current flow path between them, and so inter-electrode impedance, can be well defined and can be characterised according to pre-determined criteria depending on the hydration level. For example, the impedance can be characterised to indicate whether the dressing is dry, moist or wet. Alternatively, the impedance may be characterised, so that a measure of it provides an indication as to whether the dressing needs to be changed. By having a plurality of pair of electrodes, the hydration level across the dressing can be mapped and monitored as a function of time. To further ensure that the current paths are well defined and to limit any possible interference, the pairs of electrodes may be spaced relatively far apart from each other or insulated to prevent inter-pair current flow.

In use, an impedance meter (not shown) can be attached or applied to any of the pairs of terminals, for example, 20a, 20b to measure the impedance of the dressing/exudates solution between the corresponding electrodes, i.e. 18a and 18b. Because the electrode pairs in FIG. 1 are embedded between different layers of the dressing 10, taking measurements using each of these pairs allows a picture of the moisture through the dressing to be obtained. As noted above, to ensure that the current path between electrodes in any one of the pairs is well defined and to limit any possible interference, the pairs of electrodes are spaced relatively far apart from each other. Additionally or alternatively, in use the impedance measurements are taken individually, so that at any one time, current is only applied between a single pair of electrodes.

Figure 2:
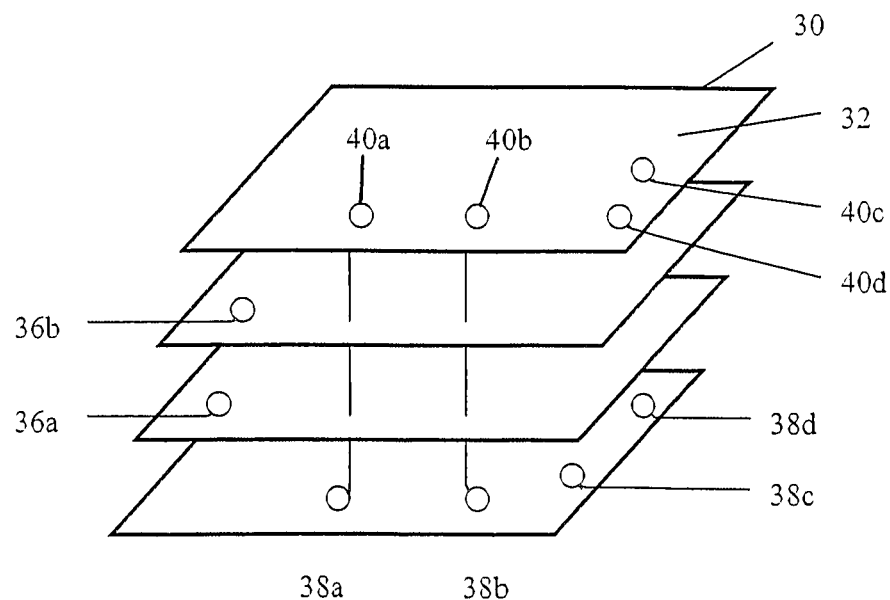
FIG. 2 is a view of a second dressing.

FIG. 2 shows an alternative dressing 30. This has an upper external surface 32, a wound contact surface 34 and two gauze layers 36a, 36b. In this case the electrodes 38, of which four are shown 38a-38d, are all positioned to take a reading from different locations within the same part/layer of the dressing, between wound contact surface 34 and the first gauze layer 36a. Each of the electrode pairs terminate at terminals 40, i.e. the first electrode pair 38a, 38b terminates at a first pair of terminals 40a, 40b etc. As the electrode pairs measure impedance within substantially the same region or layer of the dressing 30, an indication of moisture across the dressing 30 can be obtained. Again, because the electrodes of FIG. 2 are paired for the purposes of measuring the impedance of the dressing, the current flow path between them, and so inter-electrode impedance, can be well defined and can be characterised depending on the hydration level according to pre-determined criteria.

Figure 3:
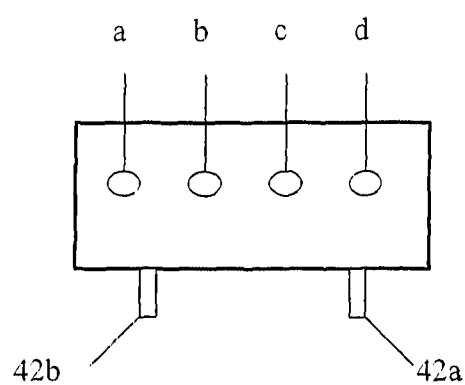
FIG. 3 is a front view of a handheld meter for use with the dressings of FIGS. 1 and 2.

When a dressing 10, 30 is applied to a patient, its impedance can be measured using a hand-held meter such as that shown in FIG. 3. This has electrodes 42a, 42b. These are spaced apart by the same amount as the pairs of terminals 20, 40 on the upper surface of the dressing, so that they can be used to take a reading from any of these terminals. The meter also includes a series of lights a-d. These lights give a visual indication of the impedance measured at a particular pair of terminals. If only light a is lit the impedance is low indicating the dressing 50 is moist at that particular location. If two or three lights are lit this indicates uniformity of moisture across all three locations. This is desirable for healing. If not it may be that some areas are drying out and the carer needs to decide if it is time to change the dressing. Clinical guidance for different wounds will be given with the instruction leaflet. If all the lights a to d are lit this indicates that at that particular location the dressing is dry and is not contributing to successful wound healing, and the dressing should be changed.

Figure 4:
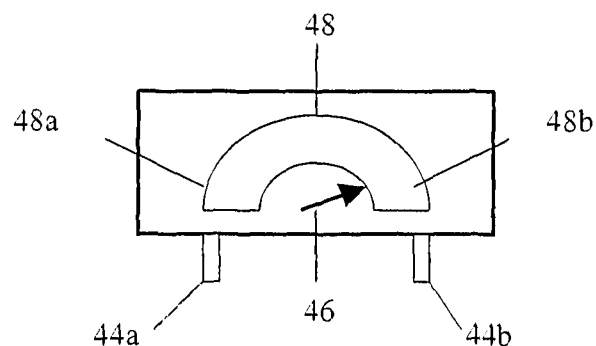
FIG. 4 is a front view of another handheld meter for use with the dressings of FIGS. 1 and 2.

FIG. 4 shows another meter that could be used. This includes colmectors/electrodes 44a, 44b adapted to measure readings from any of the pairs of terminals of FIG. 1 or FIG. 2. In this case the reading obtained is displayed using a needle 46, which indicates on a scale 48 a level of impedance. The scale 48 is divided into two zones. The first zone 48a indicates an acceptable level of moisture in the dressing to promote wound healing whereas zone 48b indicates the dressing should be changed.

The sensor arrays of FIG. 1 and 2 are designed to have localised paired electrode of a few square mm placed a few mm apart. Electrode pairs may be separated from each other by a few millimetres again to provide information on different locations. Electrical manipulation of the voltage on the electrodes through the meter could allow for very close spacing of pairs if required. Electrodes could be smaller than this and placed closer together, even to the scale of micro- and nano-electrodes for wearable or lightweight monitoring systems. Voltage is applied across the electrode pair being interrogated for impedance and at no other pairs ensuring current flow is only between selected electrode pair. The electric field direction between the electrodes favours a short current path. If there is liquid present locally it will always short circuit these electrodes and the preferred current path will be directly from electrode to electrode over the short distance separating them, ensuring local measurement of wetness. As the dressing or wound to dressing interface dries this path will become more resistive or higher impedance but current will still seek the shortest and easiest path. If parts of the path have dried out then no current can flow or high impedance will be measured between the paths. Frequency selection for measurement can also ensure that local liquid paths are preferably measured.

As well as allowing a measure of hydration to be determined, providing electrodes within a wound dressing allows the possibility of analysing the composition of the exudates that exude from that wound. To do this, an electrochemical analysis machine can be attached to the electrodes. These types of analyser are known in the art and so will not be described in detail. Such analysers have, however, not to date been used to provide an in-situ analysis of a wound exudate. Used in conjunction with the wound dressing in which the invention is embodied, these analysers provide a useful mechanism for allowing the nature of the fluid emitted from a wound to be monitored and so the healing process.

The sensor pairs of the present invention could also be used under voltage control for the detection of changes in the wound exudate. Firstly, by correct selection of short applications of different levels of d.c. voltage or by the application of voltage sweeps known as cyclic voltammetry, it would be possible to determine the presence of specific molecules or ions in the exudate. These could be molecules or ions that are markers for wound recovery or markers of wound degradation. Similarly the techniques of a.c. or d.c. impedance can be utilised on the sensor array to detect specific bacteria, microbes or other cells which yield specific information about the local presence of entities, which can be indicative of wound healing or wound infection.

To obtain a measure of the dressing moisture, it is necessary to fit the correct impedance circuits to a model of the wound dressing, taking account of the complex nature of impedance, Z, i.e.

$$Z = Z' + jZ''$$

Where Z' is the resistive component of impedance and Z" the reactive component of impedance. By using frequency analysis and mathematics, the system can be modelled as well as physically measured under different conditions. This allows the selection of voltages and frequencies where hydration may be safely measured locally as total impedance (for a more simple meter to use in medical practice) without the introduction of adverse electrochemical by-products that might affect tissue in the healing wound or destroy the electrodes themselves.

Figure 5:
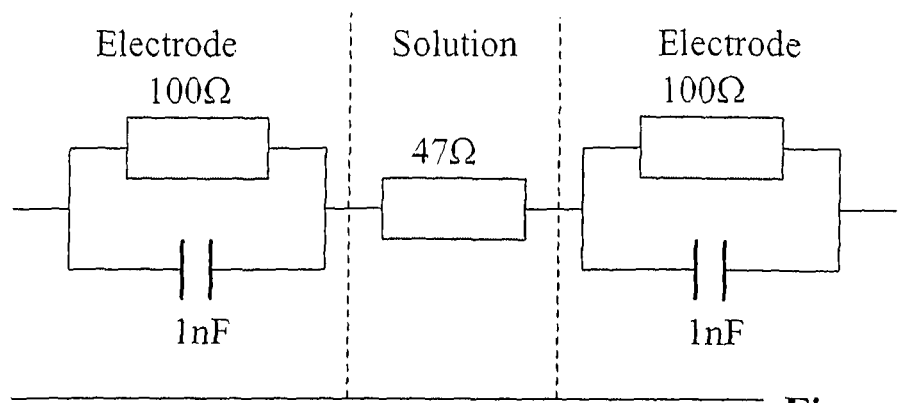
FIG. 5 is an equivalent circuit representing the measurement of a dressing impedance using two paired electrodes.
Figure 6:
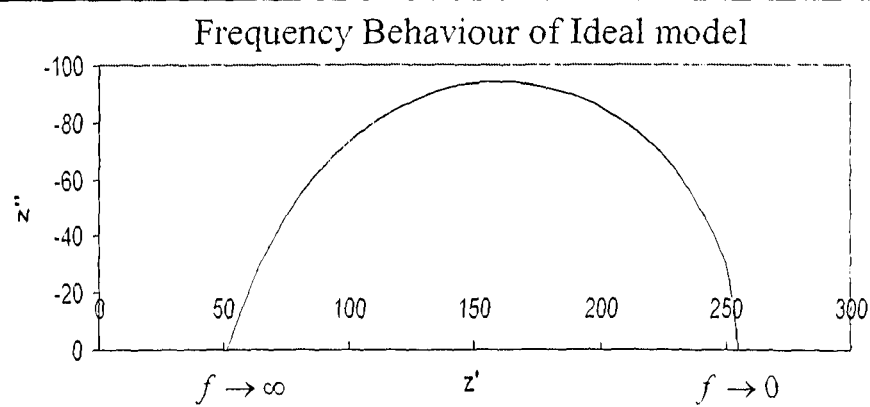
FIG. 6 is a graph showing the impedance between two electrodes as a function of frequency.

FIG. 5 shows an example of a circuit model for the paired electrodes when applied to or embedded within a dressing. In this, each electrode is represented by a resistance of 100 ohms in parallel with a 100 nanofarad capacitance, and the solution between them is represented by a resistance of about 47 ohms. Of course, the solution resistance can be very low if there is a good fluid layer between the electrodes, i.e. if the system is wet, and would increase as the system dries out. FIG. 6 shows a frequency response obtained from a measurement of a sensor pair in conducting fluid. In practice, dressing hydration may be measured over a range of different frequencies and voltages, so that the optimum and/or most practical measurement conditions can be established.

FIG. 7 shows a test rig 50 for measuring wound dressing hydration. This includes a test bed 52 with a test bed surface 54. On the test bed surface 54 there is a channel 56 and monitoring means 58a to 58i. The test rig 50 also includes a pump 60, which supplies an ionic fluid (not shown) from a reservoir 61 through a pipe 62 to the channel 66. Each of the monitoring means 58a-58i includes a pair of surface electrodes 68a and 68b (shown only with respect to the first monitoring means 58a for clarity). Each of these electrodes 68a, 68b is connected to a wire 70a, 70b which leads to an impedance meter 72. A perspective view of the first monitoring means 18a is shown in FIG. 8a with the surface electrodes 68a, 68b indicated. Alternatively, simple wire electrodes could be used, as shown in FIG. 8b. These wire electrodes would protrude from the monitoring means and the test bed surface 54 into a dressing to allow measurement of impedance at a particular depth within the dressing rather than on the surface.

In use, a dressing (not shown) is applied to the test bed surface 54 and a measurement of impedance of the dry dressing is taken from the impedance meter 72 based on the readings of the monitoring means 58a-58i. This is done using an a.c. signal of any suitable frequency, typically several kilohertz. Ionic fluid is then pumped from the pump reservoir 61 by the pump 60 through the pipe 62 and into the channel 56. The flow of ionic fluid through the channel 56 represents exudate being emitted by a wound. As the dressing becomes saturated, further readings of impedance, as measured by the monitoring means 58a-58i are taken from the impedance meter 72. After a period of time the dressing will start to dry out. Again through this drying period measurements of impedance are taken.

Figure 9:
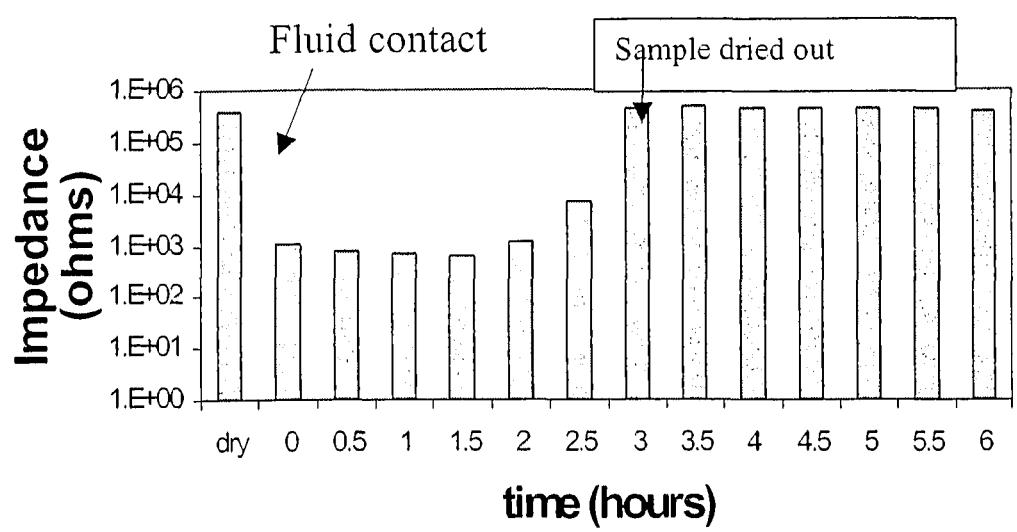
FIG. 9 is a plot showing impedance over time for a dressing measured on the test rig of FIG. 7.

FIG. 9 shows a graph of impedance against time as measured by the monitoring means 58a-58i. This graph shows three stages. The first stage is the initial wetting of the bandage by the ionic fluid and shows a rapid decrease in impedance. The second stage is a period when the impedance remains low and the dressing is working satisfactorily. However, at stage three the dressing's useful life is over as it has dried out. This can be identified by the sharp increase in the measured impedance, and subsequent constant value. Because of the readily identifiable transition between wet and dry, the impedance can be used to show that the dressing should be changed, in this example between two and three hours after application, to maintain an optimum wound healing environment.

FIGS. 10 and 11 illustrate impedance measurements from a study of five hydrofibre dressings V1 to V5 and five foam dressings T1 to T5 respectively, each monitored over a twenty-four hour period by ac impedance at low voltages. In this case, a frequency of 1 kHz and voltage of 200 mV was used. However other frequencies may be used and in general lower voltages are preferred as they prevent the excessive occurrence of localised electrochemical reactions that may affect the electrode composition or the composition of the wound fluid. In this example, eight sensor pairs were used on the test rig to measure hydration levels. Also, a temperature sensor was used to measure the dressing temperature. FIGS. 10 and 11 show the wetness status of the dressing as a colour code corresponding to the level of hydration measured at the local sensor pair. T denotes the position of a temperature sensor. F denotes that fluid was flowing into the dressing to mimic wound exudate in the first eight hours of the experiment. The numbers 1 to 8 refer to the position of the sensor pairs detecting local impedance, and so the hydration status. The impedance band for each level was selected by frequency analysis and real time experimentation with different levels of liquid in dressings. Thus, a complete profile of hydration at the interface between the wound and dressing was obtained, in a manner important for monitoring of healing.

The system and method in which the present invention is embodied use a selected low voltage and optimum frequency that will not cause local electrochemical changes in the system. This means that the electrodes can be used to monitor the dressing and wound over long periods of time from wet through optimum to dry environments. The invention links level of hydration both in the dressing and at the critical wound-to-dressing interface to specific clinical conditions in the wound—maceration, optimal healing and dryness (dressing adhesion to delicate tissue).

Figure 12:
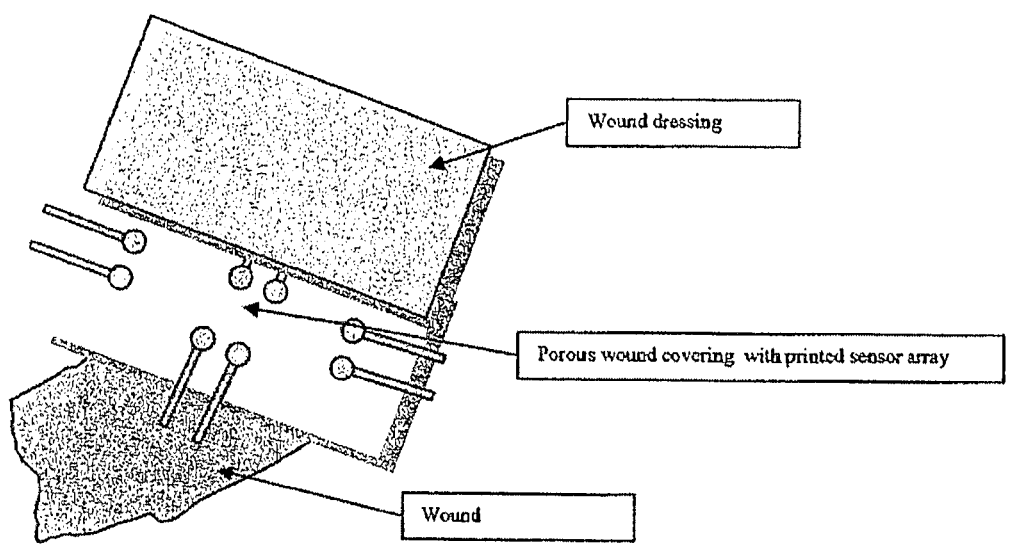
FIG. 12 is a schematic view of a dressing insert for use with a conventional wound dressing.

A skilled person will appreciate that variations of the disclosed arrangements are possible without departing from the invention. For example, rather than embedding the electrodes into a wound dressing, they could instead be included in a disposable sensor array insert suitable for use with any dressing. In this case, the sensor array could be printed onto a very porous film, typical of a light wound absorbance material, and placed underneath the dressing. An example of this is shown in FIG. 12. As before, the sensors could be made of any conducting material and printed on to any disposable porous film suitable for use with wounds such as gauze. The sensor array could be screen printed or otherwise fabricated.

As another option, the array may be arranged so that a current flow path is provided between paired electrodes in the presence of exudate, but substantially no current flow path exists between pairs of electrodes regardless of the presence of exudate. For example, the array could be insulated in regions over predetermined pairs of electrodes in such a way as to ensure preferential local hydration measurements between those electrodes, without destroying the overall porosity of the insert sheet or dressing and without the destroying fluid balance and transmission of the dressing.

Also, more electrode pairs could be used to allow the impedance to be measured across layers of the dressing and between layers of the dressing so that a full three-dimensional picture could be obtained. In addition, whilst the discussion of this invention refers to the use of impedance measurement, it will be understood by a skilled person that impedance is linked to a number of parameters mathematically. Specifically admittance, conductance, susceptance and conductivity are all examples of parameters that can be derived mathematically from the measurement of impedance. Therefore the principles inherent in this invention include the measurement of admittance, conductance, susceptance and conductivity as well as other parameters linked to the impedance measurement. Furthermore, it will be obvious to the skilled person that the systems and techniques described herein may also be applied to similar pads or dressings, such as nappies for babies or incontinence pads. Accordingly, the above description of the specific embodiment is made by way of example only and not for the purposes of limitation. It will be clear to the skilled person that minor modifications may be made without significant changes to the operation described.

The invention claimed is:

1. A wound dressing that includes a plurality of paired electrodes disposed at a plurality of predetermined locations, the plurality of paired electrodes including at least a first set of paired electrodes and a second set of paired electrodes, wherein the plurality of paired electrodes allow an electrical property or characteristic of a portion of the dressing to be measured between electrodes of the first set of paired electrodes independently from the second set of paired electrodes when a current is applied between the electrodes of the first set of paired electrodes to independently measure the area of the dressing between the electrodes of the first set of paired electrodes, wherein between the electrodes of the first set of paired electrodes there is a current flow path, and between the first set of paired electrodes and the second set of paired electrodes there is substantially no current flow path and wherein between the electrodes of each set of paired electrodes there is a path that allows current to flow in the presence of wound exudate.

2. A wound dressing according to claim 1, wherein the electrodes are embedded within the dressing.

3. A wound dressing according to claim 1, wherein the electrodes are on a surface of the dressing.

4. A wound dressing according to claim 1, wherein the electrodes are wire or printed electrodes.

5. A wound dressing according to claim 1, wherein the electrodes are made of silver/silver chloride.

6. A wound dressing according to claim 1, wherein the electrodes include terminals for connecting to an impedance meter or electrochemical analysis instrument.

7. An insert for use with a wound dressing, the insert having a plurality of paired electrodes, the plurality of paired electrodes including at least a first set of paired electrodes and a second set of paired electrodes, wherein the plurality of paired electrodes allow an electrical property or characteristic of a portion of the dressing to be measured between electrodes of the first set of paired electrodes independently from the second set of paired electrodes when a current is applied between the electrodes of the first set of paired electrodes to independently measure the area of the dressing between the electrodes of the first set of paired electrodes, wherein between the electrodes of the first set of paired electrodes there is a current flow path, and between the first set of paired electrodes and the second set of paired electrodes there is substantially no current flow path and wherein between the electrodes of each set of paired electrodes there is a path that allows current to flow in the presence of wound exudate.

8. An insert as claimed in claim 7 wherein the plurality of paired electrodes are on a porous film.

9. A method for measuring wound dressing hydration, wherein the wound dressing includes at least one pair of embedded electrodes, the method comprising:
    applying an ac signal between the electrodes of the at least one pair of embedded electrodes, the at least one pair of embedded electrodes being in contact with the wound dressing;
    measuring total impedance of material of at least one of the dressing or any exudate or wound substances present between the embedded electrodes using the ac signal;
    comparing the measured impedance with predetermined hydration level criteria for each of at least three hydration categories including dry, moist and wet, the predetermined hydration level criteria for each of the at least three hydration categories being different relative to one another; and
    characterizing the hydration of the dressing into one of the at least three hydration categories according to the predetermined hydration level criteria and the measured impedance.

10. A method as claimed in claim 9 involving analyzing the constituents of a fluid in the dressing using the impedance measured.

11. A method as claimed in claim 9 comprising monitoring the impedance as a function of time.

12. A method as claimed in claim 9 comprising measuring the impedance at a plurality of locations to provide a three-dimensional moisture distribution.

13. A method as claimed in claim 9 comprising varying the frequency and/or voltage of the ac signal to select optimum measurement conditions.

14. A method as claimed in claim 9 comprising using a dc signal in addition to the ac signal.

15. A method for measuring wound dressing hydration using an insert that includes at least one pair of electrodes and is adapted for use with the wound dressing, the method comprising:
    disposing the insert on the wound dressing wherein the at least one pair of electrodes are in contact with the wound dressing;
    applying an ac signal between the electrodes of the at least one pair of electrodes, the at least one pair of electrodes being in contact with the wound dressing;
    measuring total impedance of material of at least one of the dressing or any exudate or wound substances present between the electrodes using the ac signal; and
    comparing the measured impedance with predetermined hydration level criteria for each of at least three hydration categories including dry, moist and wet, the predetermined hydration level criteria for each of the at least three hydration categories being different relative to one another; and
    characterizing the hydration of the dressing into one of the at least three hydration categories according to the predetermined hydration level criteria and the measured impedance.

* * * * *

UNITED STATES PATENT AND TRADEMARK OFFICE
CERTIFICATE OF CORRECTION

PATENT NO. : 9,526,439 B2
APPLICATION NO. : 11/578526
DATED : December 27, 2016
INVENTOR(S) : Connolly et al.

Page 1 of 1

It is certified that error appears in the above-identified patent and that said Letters Patent is hereby corrected as shown below:

On the Title Page

"(12)  United Sates Patent
        Connelly et al."
Should read:
--(12)  United States Patent
        Connolly et al.--

"(75) Inventors: Patricia Connelly"
Should read:
--(75) Inventors: Patricia Connolly--

Signed and Sealed this
Sixteenth Day of May, 2017

Michelle K. Lee
*Director of the United States Patent and Trademark Office*